United States Patent
Watson et al.

(10) Patent No.: US 9,066,660 B2
(45) Date of Patent: Jun. 30, 2015

(54) SYSTEMS AND METHODS FOR HIGH-PASS FILTERING A PHOTOPLETHYSMOGRAPH SIGNAL

(75) Inventors: James N. Watson, Dunfermline (GB); Paul Stanley Addison, Edinburgh (GB)

(73) Assignee: Nellcor Puritan Bennett Ireland, Galway (IE)

( * ) Notice: Subject to any disclaimer, the term of this patent is extended or adjusted under 35 U.S.C. 154(b) by 1022 days.

(21) Appl. No.: 12/568,946

(22) Filed: Sep. 29, 2009

(65) Prior Publication Data

US 2011/0077531 A1   Mar. 31, 2011

(51) Int. Cl.
*A61B 5/021* (2006.01)
*A61B 5/024* (2006.01)
(Continued)

(52) U.S. Cl.
CPC ............. *A61B 5/021* (2013.01); *A61B 5/02416* (2013.01); *A61B 5/14551* (2013.01); *A61B 5/7239* (2013.01)

(58) Field of Classification Search
CPC ...................... A61B 5/02125; A61B 5/021416; A61B 5/024; A61B 5/021; A61B 5/02416; A61B 5/14551; A61B 5/7239
USPC .................................................. 600/485–507
See application file for complete search history.

(56) References Cited

U.S. PATENT DOCUMENTS

| | | |
|---|---|---|
| 3,835,840 A | 9/1974 | Mount |
| 4,561,447 A | 12/1985 | Kawamura et al. |
| 4,621,643 A | 11/1986 | New, Jr. et al. |

(Continued)

FOREIGN PATENT DOCUMENTS

| | | |
|---|---|---|
| CN | 122384 | 7/1999 |
| CN | 154031 | 10/2004 |

(Continued)

OTHER PUBLICATIONS

Bank, Alan J., Kaiser, Daniel R., "Smooth Muscle Relaxation: Effects on Arterial Compliance, Distensibility, Elastic modulus, and Pulse Wave Velocity," Hypertension, vol. 32, No. 2, Aug. 1998, pp. 356-359.

(Continued)

*Primary Examiner* — Patricia Mallari
*Assistant Examiner* — Eric Messersmith
(74) *Attorney, Agent, or Firm* — Shvarts & Leiz LLP

(57) ABSTRACT

According to embodiments, systems and methods for high-pass filtering a plethysmograph or photoplethysmograph (PPG) signal are disclosed. A sensor or probe may be used to obtain a plethysmograph or PPG signal from a subject. The sensor may be placed at any suitable location on the body, e.g., the forehead, finger, or toe. The PPG signal generated by the sensor may be high-pass filtered to disambiguate certain features of the PPG signal, including one or more characteristic points. The cut-off frequency for the high-pass filter may be greater than 0.75 Hz and less than 15 Hz. The cut-off frequency for the high-pass filter may be selected to be greater than the subject's computed pulse rate. These characteristic points on the filtered PPG signal may be used to compute non-invasive blood pressure measurements continuously or on a periodic basis. For example, the time difference between two or more characteristic points in a high-pass filtered version of the generated PPG signal may be computed. The time difference may be used to compute non-invasive blood pressure measurements continuously or on a periodic basis.

17 Claims, 7 Drawing Sheets

(51) Int. Cl.
*A61B 5/1455* (2006.01)
*A61B 5/00* (2006.01)

(56) References Cited

U.S. PATENT DOCUMENTS

| | | |
|---|---|---|
| 4,676,253 A | 6/1987 | Newman et al. |
| 4,700,708 A | 10/1987 | New, Jr. et al. |
| 4,714,080 A | 12/1987 | Edgar, Jr. et al. |
| 4,729,382 A | 3/1988 | Schaffer et al. |
| 4,770,179 A | 9/1988 | New, Jr. et al. |
| 4,796,636 A | 1/1989 | Branstetter et al. |
| 4,830,017 A | 5/1989 | Perry et al. |
| 4,836,213 A | 6/1989 | Wenzel et al. |
| 4,854,327 A | 8/1989 | Kunig |
| 4,898,176 A | 2/1990 | Petre |
| 4,913,150 A | 4/1990 | Cheung et al. |
| 4,924,871 A | 5/1990 | Honeyager |
| 4,928,700 A | 5/1990 | Harada |
| 4,942,877 A | 7/1990 | Sakai et al. |
| 4,951,679 A | 8/1990 | Harada |
| 4,976,268 A | 12/1990 | Kurosawa et al. |
| 4,987,900 A | 1/1991 | Eckerle et al. |
| 5,058,588 A | 10/1991 | Kaestle |
| 5,065,765 A | 11/1991 | Eckerle et al. |
| 5,069,213 A | 12/1991 | Polczynski |
| 5,103,831 A | 4/1992 | Niwa |
| 5,105,815 A | 4/1992 | Hall et al. |
| 5,119,824 A | 6/1992 | Niwa |
| 5,131,400 A | 7/1992 | Harada et al. |
| 5,163,328 A | 11/1992 | Holland et al. |
| 5,170,796 A | 12/1992 | Kobayashi |
| 5,176,143 A | 1/1993 | Eckerle et al. |
| 5,178,154 A | 1/1993 | Ackmann et al. |
| 5,179,956 A | 1/1993 | Harada et al. |
| 5,204,922 A | 4/1993 | Weir et al. |
| 5,238,000 A | 8/1993 | Niwa |
| 5,241,964 A | 9/1993 | McQuilkin |
| 5,255,686 A | 10/1993 | Takeda et al. |
| 5,259,381 A | 11/1993 | Cheung et al. |
| 5,267,562 A | 12/1993 | Ukawa et al. |
| 5,269,312 A | 12/1993 | Kawamura et al. |
| 5,289,823 A | 3/1994 | Eckerle |
| 5,309,917 A | 5/1994 | Wang et al. |
| 5,348,005 A | 9/1994 | Merrick et al. |
| 5,365,066 A | 11/1994 | Krueger, Jr. et al. |
| 5,431,159 A | 7/1995 | Baker et al. |
| 5,450,852 A | 9/1995 | Archibald et al. |
| 5,467,771 A | 11/1995 | Narimatsu et al. |
| 5,490,506 A | 2/1996 | Takatani et al. |
| 5,494,043 A | 2/1996 | O'Sullivan et al. |
| 5,497,779 A | 3/1996 | Takaya et al. |
| 5,505,209 A | 4/1996 | Reining |
| 5,533,511 A | 7/1996 | Kaspari et al. |
| 5,535,753 A | 7/1996 | Petrucelli et al. |
| 5,562,621 A | 10/1996 | Claude et al. |
| 5,564,427 A | 10/1996 | Aso et al. |
| 5,575,284 A | 11/1996 | Athan et al. |
| 5,617,868 A | 4/1997 | Harada et al. |
| 5,640,964 A | 6/1997 | Archibald et al. |
| 5,649,542 A | 7/1997 | Archibald et al. |
| 5,649,543 A | 7/1997 | Hosaka et al. |
| 5,660,567 A | 8/1997 | Nierlich et al. |
| 5,676,140 A | 10/1997 | Ukawa et al. |
| 5,682,898 A | 11/1997 | Aung et al. |
| 5,685,301 A | 11/1997 | Klomhaus |
| 5,685,316 A | 11/1997 | Schookin et al. |
| 5,704,362 A | 1/1998 | Hersh et al. |
| 5,709,212 A | 1/1998 | Sugo et al. |
| 5,720,292 A | 2/1998 | Poliac |
| 5,722,414 A | 3/1998 | Archibald et al. |
| 5,738,103 A | 4/1998 | Poliac |
| 5,743,856 A | 4/1998 | Oka et al. |
| 5,755,669 A | 5/1998 | Ono et al. |
| 5,758,644 A | 6/1998 | Diab et al. |
| 5,762,610 A | 6/1998 | Narimatsu et al. |
| 5,766,125 A | 6/1998 | Aoyagi et al. |
| 5,772,601 A | 6/1998 | Oka et al. |
| 5,772,602 A | 6/1998 | Sakai et al. |
| 5,776,071 A | 7/1998 | Inukai et al. |
| 5,779,630 A | 7/1998 | Fein et al. |
| 5,783,821 A | 7/1998 | Costello, Jr. |
| 5,785,659 A | 7/1998 | Caro et al. |
| 5,791,347 A | 8/1998 | Flaherty et al. |
| 5,797,395 A | 8/1998 | Martin |
| 5,797,850 A | 8/1998 | Archibald et al. |
| 5,810,736 A | 9/1998 | Pail |
| 5,823,950 A | 10/1998 | Diab et al. |
| 5,827,181 A | 10/1998 | Dias et al. |
| 5,827,182 A | 10/1998 | Raley et al. |
| 5,830,131 A | 11/1998 | Caro et al. |
| 5,832,924 A | 11/1998 | Archibald et al. |
| 5,833,618 A | 11/1998 | Caro et al. |
| 5,848,970 A | 12/1998 | Voss et al. |
| 5,857,975 A | 1/1999 | Golub |
| 5,873,834 A | 2/1999 | Yanagi et al. |
| 5,891,024 A | 4/1999 | Jarman et al. |
| 5,891,025 A | 4/1999 | Buschmann et al. |
| 5,904,654 A | 5/1999 | Wohltmann et al. |
| 5,921,921 A | 7/1999 | Potratz et al. |
| 5,922,607 A | 7/1999 | Bernreuter |
| 5,924,982 A | 7/1999 | Chin |
| 5,941,828 A | 8/1999 | Archibald et al. |
| 5,964,711 A | 10/1999 | Voss et al. |
| 5,987,343 A | 11/1999 | Kinast |
| 5,995,855 A | 11/1999 | Kiani et al. |
| 6,002,952 A | 12/1999 | Diab et al. |
| 6,004,274 A | 12/1999 | Nolan et al. |
| 6,007,492 A | 12/1999 | Goto et al. |
| 6,011,986 A | 1/2000 | Diab et al. |
| 6,022,320 A | 2/2000 | Ogura et al. |
| 6,027,452 A | 2/2000 | Flaherty et al. |
| 6,027,453 A | 2/2000 | Miwa et al. |
| 6,027,455 A | 2/2000 | Inukai et al. |
| 6,044,283 A | 3/2000 | Fein et al. |
| 6,045,509 A | 4/2000 | Caro et al. |
| 6,064,899 A | 5/2000 | Fein et al. |
| 6,067,462 A | 5/2000 | Diab et al. |
| 6,078,833 A | 6/2000 | Hueber |
| 6,083,171 A | 7/2000 | Ono et al. |
| 6,095,987 A | 8/2000 | Shmulewitz et al. |
| 6,133,994 A | 10/2000 | Mathews et al. |
| 6,135,966 A | 10/2000 | Ko |
| 6,151,107 A | 11/2000 | Schollermann et al. |
| 6,157,850 A | 12/2000 | Diab et al. |
| 6,159,157 A | 12/2000 | Archibald et al. |
| 6,161,038 A | 12/2000 | Schookin et al. |
| 6,186,954 B1 | 2/2001 | Narimatsu |
| 6,186,955 B1 | 2/2001 | Baura |
| 6,190,382 B1 | 2/2001 | Ormsby et al. |
| 6,196,974 B1 | 3/2001 | Miwa |
| 6,217,524 B1 | 4/2001 | Orr et al. |
| 6,226,540 B1 | 5/2001 | Bernreuter et al. |
| 6,227,196 B1 | 5/2001 | Jaffe et al. |
| 6,228,034 B1 | 5/2001 | Voss et al. |
| 6,241,661 B1 | 6/2001 | Schluess et al. |
| 6,241,679 B1 | 6/2001 | Curran |
| 6,245,022 B1 | 6/2001 | Archibald et al. |
| 6,251,081 B1 | 6/2001 | Narimatsu |
| 6,263,222 B1 | 7/2001 | Diab et al. |
| 6,280,381 B1 | 8/2001 | Malin et al. |
| 6,292,689 B1 | 9/2001 | Wallace et al. |
| 6,293,915 B1 | 9/2001 | Amano et al. |
| 6,298,252 B1 | 10/2001 | Kovach et al. |
| 6,299,582 B1 | 10/2001 | Brockway et al. |
| 6,332,867 B1 | 12/2001 | Chen et al. |
| 6,349,228 B1 | 2/2002 | Kiani et al. |
| 6,350,242 B1 | 2/2002 | Doten et al. |
| 6,351,658 B1 | 2/2002 | Middleman et al. |
| 6,356,774 B1 | 3/2002 | Bernstein et al. |
| 6,371,921 B1 | 4/2002 | Caro et al. |
| 6,377,829 B1 | 4/2002 | Al-Ali |
| 6,397,091 B2 | 5/2002 | Diab et al. |
| 6,421,549 B1 | 7/2002 | Jacques |
| 6,443,905 B1 | 9/2002 | Nissila et al. |

(56) References Cited

U.S. PATENT DOCUMENTS

| | | |
|---|---|---|
| 6,463,310 B1 | 10/2002 | Swedlow et al. |
| 6,463,311 B1 | 10/2002 | Diab |
| 6,471,646 B1 | 10/2002 | Thede |
| 6,471,655 B1 | 10/2002 | Baura |
| 6,501,974 B2 | 12/2002 | Huiku |
| 6,506,161 B2 | 1/2003 | Brockway et al. |
| 6,514,211 B1 | 2/2003 | Baura |
| 6,524,240 B1 | 2/2003 | Thede |
| 6,549,284 B1 | 4/2003 | Boas et al. |
| 6,553,241 B2 | 4/2003 | Mannheimer et al. |
| 6,561,986 B2 | 5/2003 | Baura et al. |
| 6,584,336 B1 | 6/2003 | Ali et al. |
| 6,587,704 B1 | 7/2003 | Fine et al. |
| 6,589,185 B1 | 7/2003 | Archibald et al. |
| 6,591,123 B2 | 7/2003 | Fein et al. |
| 6,597,933 B2 | 7/2003 | Kiani et al. |
| 6,600,940 B1 | 7/2003 | Fein et al. |
| 6,602,199 B2 | 8/2003 | Chen et al. |
| 6,602,201 B1 | 8/2003 | Hepp et al. |
| 6,606,510 B2 | 8/2003 | Swedlow et al. |
| 6,606,511 B1 | 8/2003 | Ali et al. |
| 6,618,602 B2 | 9/2003 | Levin |
| 6,626,839 B2 | 9/2003 | Doten et al. |
| 6,628,975 B1 | 9/2003 | Fein et al. |
| 6,631,281 B1 | 10/2003 | Kastle |
| 6,643,531 B1 | 11/2003 | Katarow |
| 6,645,156 B2 | 11/2003 | Oka |
| 6,658,277 B2 | 12/2003 | Wasserman |
| 6,668,183 B2 | 12/2003 | Hicks et al. |
| 6,684,090 B2 | 1/2004 | Ali et al. |
| 6,697,653 B2 | 2/2004 | Hanna |
| RE38,476 E | 3/2004 | Diab et al. |
| 6,699,194 B1 | 3/2004 | Diab et al. |
| 6,708,049 B1 | 3/2004 | Berson et al. |
| 6,711,425 B1 | 3/2004 | Reuss |
| 6,725,075 B2 | 4/2004 | Al-Ali |
| 6,760,609 B2 | 7/2004 | Jacques |
| 6,767,328 B2 | 7/2004 | Kulik |
| 6,773,397 B2 | 8/2004 | Kelly |
| 6,783,498 B2 | 8/2004 | Sackner et al. |
| 6,801,797 B2 | 10/2004 | Mannheimer et al. |
| 6,816,741 B2 | 11/2004 | Diab |
| 6,822,564 B2 | 11/2004 | Al-Ali |
| 6,826,419 B2 | 11/2004 | Diab et al. |
| 6,827,688 B2 | 12/2004 | Goto et al. |
| 6,839,580 B2 | 1/2005 | Zonios et al. |
| 6,852,083 B2 | 2/2005 | Caro et al. |
| 6,855,112 B2 | 2/2005 | Kao et al. |
| 6,863,652 B2 | 3/2005 | Huang et al. |
| 6,865,407 B2 | 3/2005 | Kimball et al. |
| 6,869,403 B2 | 3/2005 | Narimatsu et al. |
| 6,882,874 B2 | 4/2005 | Huiku |
| 6,889,153 B2 | 5/2005 | Dietiker |
| 6,929,610 B2 | 8/2005 | Forstner |
| 6,950,687 B2 | 9/2005 | Al-Ali |
| 6,996,427 B2 | 2/2006 | Ali et al. |
| 6,999,904 B2 | 2/2006 | Weber et al. |
| 7,004,907 B2 | 2/2006 | Banet et al. |
| 7,039,449 B2 | 5/2006 | Al-Ali |
| 7,043,293 B1 | 5/2006 | Baura |
| 7,044,918 B2 | 5/2006 | Diab |
| 7,070,566 B2 | 7/2006 | Medero et al. |
| 7,074,192 B2 | 7/2006 | Friedman et al. |
| 7,079,035 B2 | 7/2006 | Bock et al. |
| 7,087,025 B2 | 8/2006 | Baruch |
| RE39,268 E | 9/2006 | Merrick et al. |
| 7,120,480 B2 | 10/2006 | Chew et al. |
| 7,124,048 B2 | 10/2006 | Dietiker |
| 7,142,901 B2 | 11/2006 | Kiani et al. |
| 7,184,809 B1 | 2/2007 | Sterling et al. |
| 7,215,984 B2 | 5/2007 | Diab et al. |
| 7,215,985 B2 | 5/2007 | Petersen et al. |
| 7,215,986 B2 | 5/2007 | Diab et al. |
| 7,230,688 B1 | 6/2007 | Villarreal |
| 7,239,901 B2 | 7/2007 | Gritsenko |
| 7,248,910 B2 | 7/2007 | Li et al. |
| 7,252,636 B2 | 8/2007 | Brown |
| 7,272,425 B2 | 9/2007 | Al-Ali |
| 7,274,955 B2 | 9/2007 | Kiani et al. |
| 7,313,426 B2 | 12/2007 | Takeda et al. |
| 7,320,030 B2 | 1/2008 | Brown |
| 7,335,162 B2 | 2/2008 | Eide |
| 7,373,192 B2 | 5/2008 | Chew et al. |
| 7,376,238 B1 | 5/2008 | Rivas et al. |
| 7,390,300 B2 | 6/2008 | Inukai et al. |
| 7,390,301 B2 | 6/2008 | Skrabal et al. |
| 7,393,327 B2 | 7/2008 | Inukai et al. |
| 7,400,257 B2 | 7/2008 | Rivas |
| 7,428,432 B2 | 9/2008 | Ali et al. |
| 7,430,444 B2 | 9/2008 | Pologe et al. |
| 7,438,683 B2 | 10/2008 | Al-Ali et al. |
| 7,455,643 B1 | 11/2008 | Li et al. |
| 7,481,772 B2 | 1/2009 | Banet |
| 7,485,095 B2 | 2/2009 | Shusterman |
| 7,691,067 B2 * | 4/2010 | Westbrook et al. ........... 600/485 |
| 2001/0021803 A1 | 9/2001 | Blank et al. |
| 2002/0058876 A1 * | 5/2002 | Chen et al. ................ 600/485 |
| 2002/0103423 A1 | 8/2002 | Chin et al. |
| 2003/0073889 A1 | 4/2003 | Keilbach et al. |
| 2003/0176776 A1 | 9/2003 | Huiku |
| 2003/0195402 A1 | 10/2003 | Fein et al. |
| 2003/0197679 A1 | 10/2003 | Ali et al. |
| 2004/0006261 A1 | 1/2004 | Swedlow et al. |
| 2004/0133088 A1 | 7/2004 | Al-Ali |
| 2004/0147823 A1 | 7/2004 | Kiani et al. |
| 2004/0147824 A1 | 7/2004 | Diab et al. |
| 2004/0162472 A1 | 8/2004 | Berson et al. |
| 2004/0171920 A1 | 9/2004 | Mannheimer et al. |
| 2004/0242980 A1 | 12/2004 | Kiani et al. |
| 2004/0267103 A1 | 12/2004 | Li et al. |
| 2005/0065417 A1 | 3/2005 | Ali et al. |
| 2005/0148885 A1 | 7/2005 | Tweed et al. |
| 2005/0168722 A1 | 8/2005 | Forstner et al. |
| 2005/0192488 A1 | 9/2005 | Bryenton et al. |
| 2005/0192493 A1 | 9/2005 | Wuori |
| 2005/0222502 A1 | 10/2005 | Cooper |
| 2005/0228253 A1 | 10/2005 | Debreczeny |
| 2005/0250998 A1 | 11/2005 | Huiku |
| 2005/0251344 A1 | 11/2005 | Appel et al. |
| 2005/0261594 A1 | 11/2005 | Banet |
| 2005/0277818 A1 | 12/2005 | Myers |
| 2006/0009700 A1 | 1/2006 | Brumfield et al. |
| 2006/0020185 A1 | 1/2006 | Al-Ali |
| 2006/0030763 A1 | 2/2006 | Mannheimer et al. |
| 2006/0063992 A1 | 3/2006 | Yu et al. |
| 2006/0063993 A1 | 3/2006 | Yu et al. |
| 2006/0079945 A1 | 4/2006 | Libbus |
| 2006/0200018 A1 | 9/2006 | Al-Ali |
| 2006/0206021 A1 | 9/2006 | Diab |
| 2006/0211925 A1 | 9/2006 | Lamego et al. |
| 2006/0217614 A1 | 9/2006 | Takala et al. |
| 2006/0217628 A1 | 9/2006 | Huiku |
| 2006/0241975 A1 | 10/2006 | Brown |
| 2006/0258926 A1 | 11/2006 | Ali et al. |
| 2006/0285736 A1 | 12/2006 | Brown |
| 2006/0287603 A1 | 12/2006 | Bartnik et al. |
| 2007/0066910 A1 | 3/2007 | Inukai et al. |
| 2007/0073127 A1 | 3/2007 | Kiani et al. |
| 2007/0083093 A1 | 4/2007 | Diab |
| 2007/0100220 A1 | 5/2007 | Baker |
| 2007/0112260 A1 | 5/2007 | Diab et al. |
| 2007/0118045 A1 | 5/2007 | Naghavi et al. |
| 2007/0149883 A1 * | 6/2007 | Yesha ........................ 600/485 |
| 2007/0208236 A1 | 9/2007 | Hicks |
| 2007/0225582 A1 | 9/2007 | Diab et al. |
| 2007/0244376 A1 | 10/2007 | Wang |
| 2007/0249467 A1 | 10/2007 | Hong et al. |
| 2007/0270699 A1 * | 11/2007 | Crabtree et al. .............. 600/500 |
| 2008/0015424 A1 | 1/2008 | Bernreuter |
| 2008/0015451 A1 | 1/2008 | Hatib et al. |
| 2008/0030468 A1 | 2/2008 | Ali et al. |
| 2008/0033305 A1 | 2/2008 | Hatib et al. |
| 2008/0039701 A1 | 2/2008 | Ali et al. |
| 2008/0081969 A1 | 4/2008 | Feldman et al. |

(56) References Cited

U.S. PATENT DOCUMENTS

| | | |
|---|---|---|
| 2008/0081970 A1 | 4/2008 | Boyce et al. |
| 2008/0132798 A1 | 6/2008 | Hong et al. |
| 2008/0214903 A1 | 9/2008 | Orbach |
| 2008/0214942 A1 | 9/2008 | Oh et al. |
| 2008/0221410 A1 | 9/2008 | Campbell et al. |
| 2008/0221427 A1 | 9/2008 | Petersen |
| 2008/0221462 A1 | 9/2008 | Baker |
| 2008/0242955 A1 | 10/2008 | Uutela et al. |
| 2008/0316488 A1 | 12/2008 | Mao et al. |
| 2009/0048497 A1 | 2/2009 | Keren |
| 2009/0259116 A1* | 10/2009 | Wasserman et al. .......... 600/323 |

FOREIGN PATENT DOCUMENTS

| | | |
|---|---|---|
| EP | 0443267 | 8/1991 |
| EP | 0755221 | 1/1997 |
| EP | 793942 | 9/1997 |
| EP | 1828731 | 9/2007 |
| EP | 1877756 | 1/2008 |
| GB | 2356250 | 5/2001 |
| GB | 2356251 | 5/2001 |
| GB | 2356252 | 5/2001 |
| JP | 03225268 | 10/1991 |
| JP | 03231630 | 10/1991 |
| JP | 06142082 | 5/1994 |
| JP | 07136136 | 5/1995 |
| JP | 2001245871 | 9/2001 |
| JP | 2004113353 | 4/2004 |
| JP | 2005087405 | 4/2005 |
| WO | WO-9111137 | 8/1991 |
| WO | WO-0214793 | 2/2002 |
| WO | WO-03011127 | 2/2003 |
| WO | WO-2006124455 | 11/2006 |
| WO | WO-2007051066 | 5/2007 |
| WO | WO-2008035076 | 3/2008 |
| WO | WO-2008039195 | 4/2008 |

OTHER PUBLICATIONS

Berne, Robert M., Levy, Matthew N., eds., Physiology, 2nd edition, St. Louis, Mosby, 1988, pp. 357-681.

Brunner, John M. R., Krenis, Laurence J., Kunsman, Judith M., Sherman, Allan P., "Comparison of direct and indirect methods of measuring arterial blood pressure, part II," Medical Instrumentation, vol. 15, No. 2, Mar.-Apr. 1981, pp. 97-101.

Finkelstein, Stanley M., Cohn, Jay N., "First- and Third-Order Models for Determining Arterial Compliance," Journal of Hypertension, vol. 10, supplement 6, Aug. 1992, pp. 511-514.

Fitchett, D., Bouthier, JD, Simon, A. Ch., Levenson, JA, Safar, ME, "Forearm Arterial Compliance: The Validation of a Plethysmographic Technique for the Measurement of Arterial Compliance," Clinical Science, vol. 67, No. 1, Jul. 1984, pp. 69-72.

Fletcher, Gerald F., ed., Cardiovascular Response to Exercise, Mt. Kisco, NY, Futura Publishing Co., 1994.

Fung, YC, Biomechanics: Circulation, 2nd Edition, New York, Springer, 1997.

Geddes, LA, Handbook of Blood Pressure Measurement, Clifton, New Jersey, Humana Press, 1991.

Millasseau, Sandrine C, Guigui, Franck G, Kelly, Ronan P., Prasad, Krishna, Cockcroft, John R., Ritter, James M., Chowienczyk, Philip J., Noninvasive Assessment of the Digital Volume Pulse: Comparison with the Peripheral Pressure Pulse, Hypertension, vol. 36, No. 6, Dec. 2000, pp. 952-956.

Moyle, John TB, Hahn, Cew, Adams, Anthony P, Pulse Oximetry, Revised Edition, London, BMJ, 1998.

Nara, Andrew R., Burns, Michael P., Downs, W. Gregory, Blood Pressure, Redmond, Washington, SpaceLabs, 1989.

Nichols, Wilmer W., O'Rourke, Michael F., McDonald's Blood Flow in Arteries: Theoretic, Experimental, and Clinical Principles, 3rd Edition, Philadelphia, Lea & Febiger, 1990.

O'Rourke, Michael F., Gallagher, David E., "Pulse Wave Analysis," Journal of Hypertension, vol. 14, supplement 5, Dec. 1996, pp. S147-S157.

Takazawa, Kenji, Tanaka, Nobuhiro, Fujita, Masami, Matsuoka, Osamu, Saiki, Tokuyu, Aikawa, Masaru, Tamura, Sinobu, Ibukiyama, Chiharu, "Assessment of Vasoactive Agents and Vascular Aging by the Second Derivative of Photoplethysmogram Waveform," Hypertension, vol. 32, No. 2, Aug. 1998, pp. 365-370.

Tardy, Y, Meister, JJ, Perret F, Brunner, HR, Arditi, M, "Non-Invasive Estimate of the Mechanical Properties of Peripheral Arteries from Ultrasonic and Photoplethysmographic Measurements," Clinical Physics and Physiological Measurement, vol. 12, No. 1, pp. 39-54, Feb. 1991.

Young, Christopher C., Mark, Jonathan B., White, William, DeBree, Ashley, Vender, Jeffery S., Fleming, Andrew, "Clinical Evaluation of Continuous Noninvasive Blood Pressure Monitoring: Accuracy and Tracking Capabilities," Journal of Clinical Monitoring, vol. 11, No. 4, Jul. 1995, pp. 245-252.

* cited by examiner

SYSTEMS AND METHODS FOR HIGH-PASS FILTERING A PHOTOPLETHYSMOGRAPH SIGNAL

SUMMARY

The present disclosure relates to filtering a photoplethysmograph (PPG) signal and, more particularly, the present disclosure relates to systems and methods for high-pass filtering a PPG signal for determining non-invasive blood pressure.

In an embodiment, a probe or sensor may detect a PPG signal. This PPG signal may be used with a continuous non-invasive blood pressure (referred to herein as "CNIBP") monitoring system or pulse oximeter. For instance, the PPG signal may be analyzed and used to compute a time difference between one or more characteristic points in the detected PPG signal. From this time difference, relatively reliable and accurate blood pressure measurements may be computed on a continuous or periodic basis. Chen et al. U.S. Pat. No. 6,599,251, which is hereby incorporated by reference herein in its entirety, discloses some techniques for continuous and non-invasive blood pressure monitoring using probes or sensors that may be used in conjunction with the present disclosure.

In an embodiment, the shape of a PPG signal may be considered to be made up of the pulse wave and its many reflections throughout the circulatory system. Because of this consideration, the PPG signal may be useful in determining the blood pressure of a patient by identifying, for example, certain characteristic points in the PPG signal. The time difference between identified characteristic points in a detected PPG signal may then be used in place of an elapsed time between the arrival of corresponding points of a pulse signal relied on by two-probe or two-sensor CNIBP monitoring techniques. In some embodiments, the elapsed time between the arrival of corresponding characteristic points of a pulse signal obtained from a single probe or sensor may be used for CNIBP monitoring.

In an embodiment, to ensure an accurate identification of the characteristic points, the PPG signal may be filtered using a suitable low-pass, high-pass, or band-pass filter, or any combination thereof. This filtering may be of particular relevance for PPG signals that are measured with reflective probes or sensors in regions of the body, e.g., in the forehead, in which one or more complex paths are taken by the propagating pulse waves. The cut-off frequency for the filter may be pre-selected by a user interacting with the CNIBP monitoring system or oximeter or may be a pre-determined setting in the CNIBP monitoring system or oximeter.

Characteristic points in the PPG signal may include, for example, the turning points of the filtered PPG signal (or any suitable derivative thereof), points of inflection in the filtered PPG signal (or in any suitable derivative thereof), stationary points in the filtered PPG signal (or in any suitable derivative thereof), and any suitable peak or valley in the filtered PPG signal and/or in some derivative of the filtered PPG signal. In some embodiments, adjacent peaks (or adjacent valleys) are used as characteristic points in the PPG signal. From the measured time difference between the two or more of these characteristics points in the PPG signal, a patient's blood pressure may be monitored continuously or periodically.

In an embodiment, a PPG signal is detected and a cut-off frequency for a high-pass filter, $f_c$, is selected. In an embodiment, the cut-off frequency is selected to be greater than that of a typical pulse rate or a subject's measured or computed pulse rate. This cut-off frequency enables the filtering of the large scale morphology of each individual pulse and enhances individual features within the pulse morphology. For example, in an embodiment, the cut-off frequency is selected to be greater than 0.75 Hz and less than 15 Hz. For example, the selected cut-off frequency may be 7.5 Hz. Generally, the cut-off frequency should not be selected to be below the subject's measured or computed pulse rate. However, there is also a practical limit for the cut-off frequency. Beyond this limit, the filtered PPG signal will have almost no frequency components corresponding to the pulse morphology, yet will contain frequency components of the electrical noise from within the system that acquires the PPG signal. This practical limit may be about 15 Hz depending on the noise in the system. The detected PPG signal is then filtered using the high-pass filter, and at least one characteristic point in the filtered PPG signal are identified. In some embodiments, the characteristic points in the filtered PPG signal may include at least one stationary point or inflection point of the filtered PPG signal, a local turning point in the filtered PPG signal, two peaks in the filtered PPG signal, or any combination thereof.

In an embodiment, blood pressure measurements are then determined based at least in part on the identified characteristic points, e.g., by taking a natural logarithm of a time difference between two characteristic points, or by solving a multi-parameter equation, e.g., $p=a+b\cdot\ln(T)$ or a mathematical equivalent thereof, where p is the determined blood pressure measurement, T is a time difference determined from the identified characteristic points, and a and b are constants. In an embodiment, at least one calibration of the determined blood pressure is performed based at least in part on a known reference blood pressure measurement.

In an embodiment, a system for high-pass filtering a PPG signal used for determining a blood pressure measurement includes a sensor (e.g., a pulse oximeter) capable of generating the PPG signal and a processor. The processor may be capable of detecting the PPG signal, selecting a cut-off frequency for a high-pass filter, filtering the detected PPG signal with the high-pass filter, identifying at least one characteristic point in the filtered PPG signal, and determining, based at least in part on the identified characteristic points, the blood pressure measurement.

In an embodiment, a computer-readable medium for use in filtering a PPG signal used for determining a blood pressure measurement includes computer program instructions. The computer program instructions recorded on the computer-readable medium include instructions for detecting the PPG signal, selecting a cut-off frequency for a high-pass filter, filtering the detected PPG signal with the high-pass filter, identifying at least one characteristic point in the filtered PPG signal, and determining, based at least in part on the identified characteristic points, the blood pressure measurement.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Some CNIBP monitoring techniques utilize two probes or sensors positioned at two different locations on a subject's body. The elapsed time, T, between the arrivals of corresponding points of a pulse signal at the two locations may then be determined using signals obtained by the two probes or sensors. The estimated blood pressure, p, may then be related to the elapsed time, T, by $$p = a + b \cdot \ln(T) \tag{1}$$

where a and b are constants that may be dependent upon the nature of the subject and the nature of the signal detecting devices. Other suitable equations using an elapsed time between corresponding points of a pulse signal may also be used to derive an estimated blood pressure measurement.

Equation (1) may be used to determine the estimated blood pressure from the time difference, T, between corresponding points of a pulse signal received by two sensors or probes attached to two different locations of a subject. As described in more detail below, however, the value used for the time difference, T, in equation (1) (or in any other blood pressure equation using an elapsed time value between corresponding points of a pulse signal) may also be derived from a signal obtained from a single sensor or probe. In some embodiments, the signal obtained from the single sensor or probe may take the form of a PPG signal obtained, for example, from a CNIBP monitoring system or pulse oximeter.

A PPG signal may be used to determine blood pressure according to the present disclosure at least in part because the shape of the PPG signal may be considered to be made up of the pulse wave and its many reflections throughout the circulatory system. As such, blood pressure equations used in continuous blood pressure monitoring techniques that use sensors or probes at two locations (e.g., equation (1) above) may also be used with continuous blood pressure monitoring techniques that use only a single probe. As described in more detail below, characteristic points may be identified in a detected PPG signal. To determine blood pressure using a PPG signal, the time difference, T, in equation (1) (or in any other blood pressure equation using the time between corresponding points of a pulse signal) may then be substituted with the time between two characteristic points in a detected PPG signal.

Figure 1:
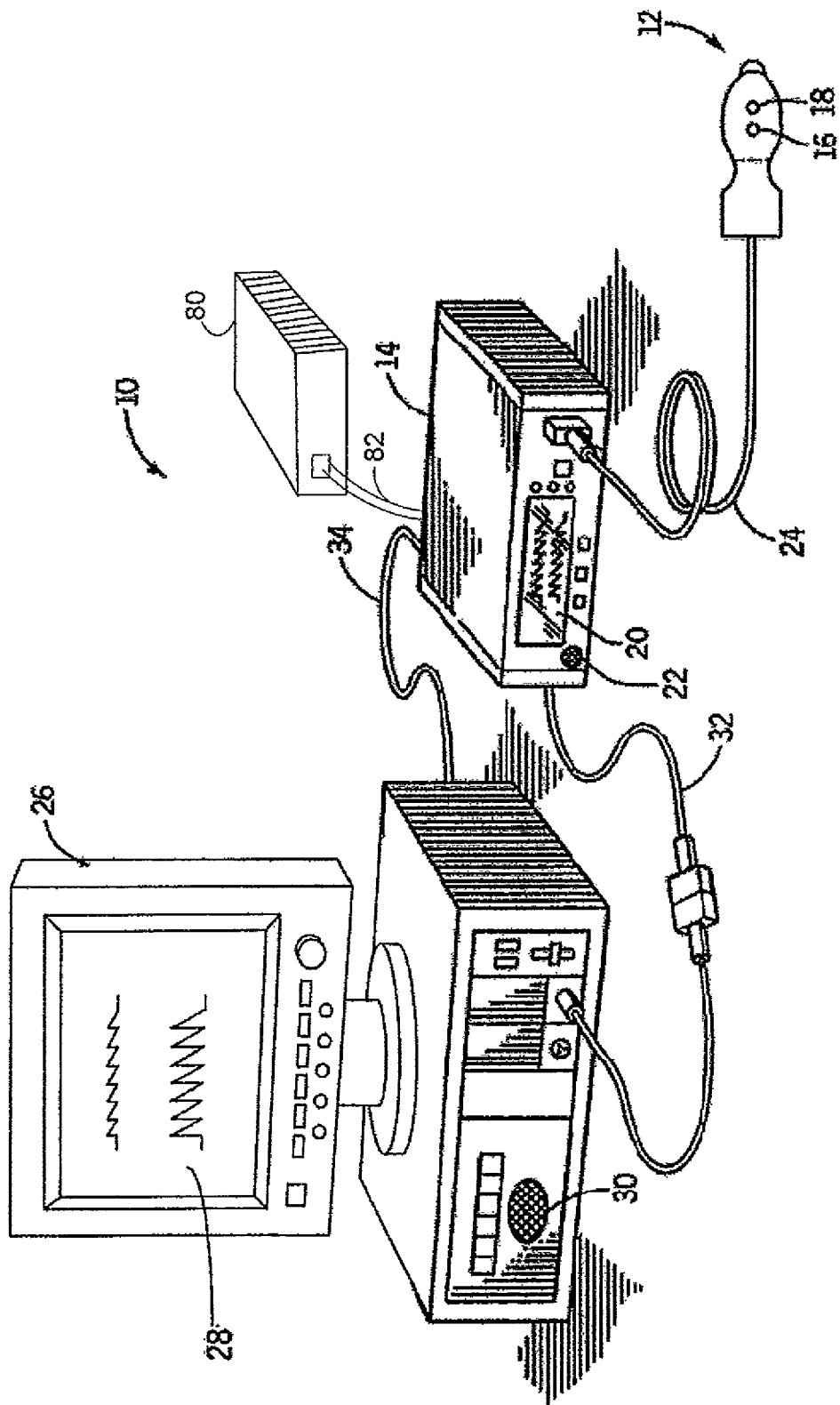
FIG. 1 shows an illustrative CNIBP monitoring system in accordance with an embodiment.

FIG. 1 is a perspective view of an embodiment of a CNIBP monitoring system 10 that may also be used to perform pulse oximetry. System 10 may include a sensor 12 and a monitor 14. Sensor 12 may include an emitter 16 for emitting light at one or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, detector 18 (e.g., a reflective sensor) may be positioned anywhere a strong pulsatile flow may be detected (e.g., over arteries in the neck, wrist, thigh, ankle, ear, or any other suitable location). In an embodiment, emitter 16 and detector 18 may be arranged so that light from emitter 16 penetrates the tissue and is reflected by the tissue into detector 18, such as a sensor designed to obtain pulse oximetry or CNIBP data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters (e.g., blood pressure) based at least in part on data received from sensor 12 relating to light emission and detection. In an alternative embodiment, the calculations may be performed on the monitoring device itself and the result of the light intensity reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multi-parameter patient monitor 26 may be configured to display an estimate of a patient's blood pressure from monitor 14, blood oxygen saturation generated by monitor 14 (referred to as an "SpO$_2$" measurement), and pulse rate information from monitor 14.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Calibration device 80, which may be powered by monitor 14, a battery, or by a conventional power source such as a wall outlet, may include any suitable blood pressure calibration device. For example, calibration device 80 may take the form of any invasive or non-invasive blood pressure monitoring or measuring system used to generate reference blood pressure measurements for use in calibrating the CNIBP monitoring techniques described herein. Such calibration devices may include, for example, an aneroid or mercury sphygmomanometer and occluding cuff, a pressure sensor inserted directly into a suitable artery of a patient, an oscillometric device or any other device or mechanism used to sense, measure, determine, or derive a reference blood pressure measurement. In some embodiments, calibration device 80 may include a manual input device (not shown) used by an operator to manually input reference blood pressure measurements obtained from some other source (e.g., an external invasive or non-invasive blood pressure measurement system).

Calibration device 80 may also access reference blood pressure measurements stored in memory (e.g., RAM, ROM, or a storage device). For example, in some embodiments, calibration device 80 may access reference blood pressure measurements from a relational database stored within calibration device 80, monitor 14, or multi-parameter patient monitor 26. The reference blood pressure measurements generated or accessed by calibration device 80 may be updated in real-time, resulting in a continuous source of reference blood pressure measurements for use in continuous or periodic calibration. Alternatively, reference blood pressure measurements generated or accessed by calibration device 80 may be updated periodically, and calibration may be performed on the same periodic cycle. In the depicted embodiments, calibration device 80 is connected to monitor 14 via cable 82. In other embodiments, calibration device 80 may be a stand-alone device that may be in wireless communication with monitor 14. Reference blood pressure measurements may then be wirelessly transmitted to monitor 14 for use in calibration. In still other embodiments, calibration device 80 is completely integrated within monitor 14.

Figure 2:
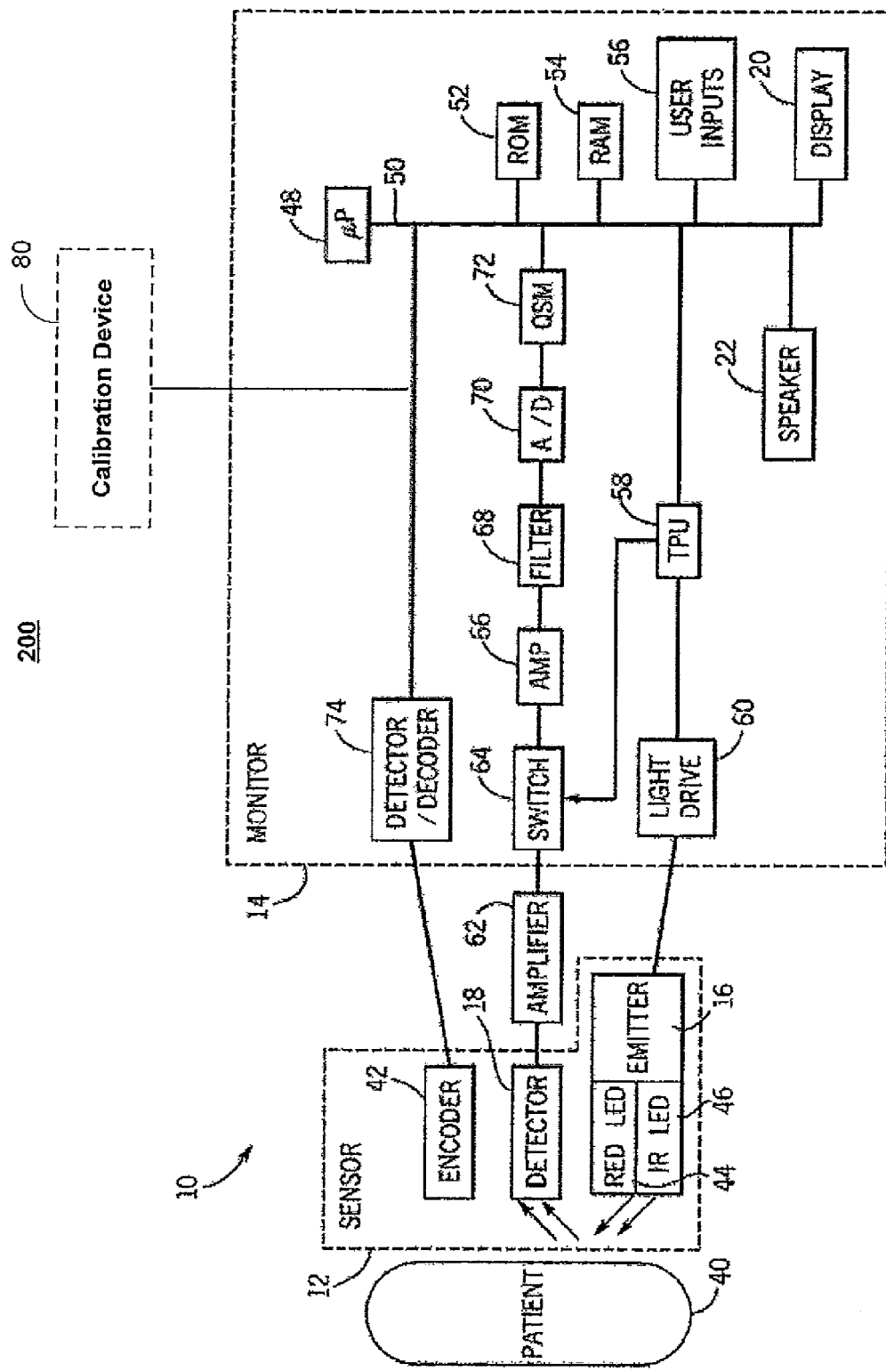
FIG. 2 is a block diagram of the illustrative CNIBP monitoring system of FIG. 1 coupled to a patient in accordance with an embodiment.

FIG. 2 is a block diagram of a CNIBP monitoring system, such as system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least one wavelength of light (e.g., RED or IR) into a patient's tissue 40. For calculating $SpO_2$, emitter 16 may include a RED light emitting light source such as RED light emitting diode (LED) 44 and an IR light emitting light source such as IR LED 46 for emitting light into the patient's tissue 40. In other embodiments, emitter 16 may include a light emitting light source of a wavelength other than RED or IR. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the emitted wavelengths (or any other suitable wavelength). Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed, reflected or scattered, less light of that wavelength is received from the tissue by the detector 18. After converting the received light to an electrical signal, detector 18 may send the signal to monitor 14, where physiological parameters may be calculated based on the absorption of one or more of the RED and IR (or other suitable) wavelengths in the patient's tissue 40.

In an embodiment, encoder 42 may contain information about sensor 12, such as what type of sensor it is (e.g., whether the sensor is intended for placement on a forehead or digit) and the wavelength or wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelength or wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelength or wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and nonremovable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as blood pressure, $SpO_2$, and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the sensor or probe is attached.

Noise (e.g., from patient movement) can degrade a CNIBP or pulse oximetry signal relied upon by a physician, without the physician's awareness. This is especially true if the monitoring of the patient is remote, the motion is too small to be observed, or the doctor is watching the instrument or other parts of the patient, and not the sensor site. Processing CNIBP or pulse oximetry (i.e., PPG) signals may involve operations that reduce the amount of noise present in the signals or otherwise identify noise components in order to prevent them from affecting measurements of physiological parameters derived from the PPG signals.

CNIBP monitoring system 10 may also include calibration device 80. Although shown external to monitor 14 in the example of FIG. 2, calibration device 80 may additionally or alternatively be internal to monitor 14. Calibration device 80 may be connected to internal bus 50 of monitor 14. As described in more detail below, reference blood pressure measurements from calibration device 80 may be accessed by microprocessor 48 for use in calibrating the CNIBP measurements.

Figure 3:
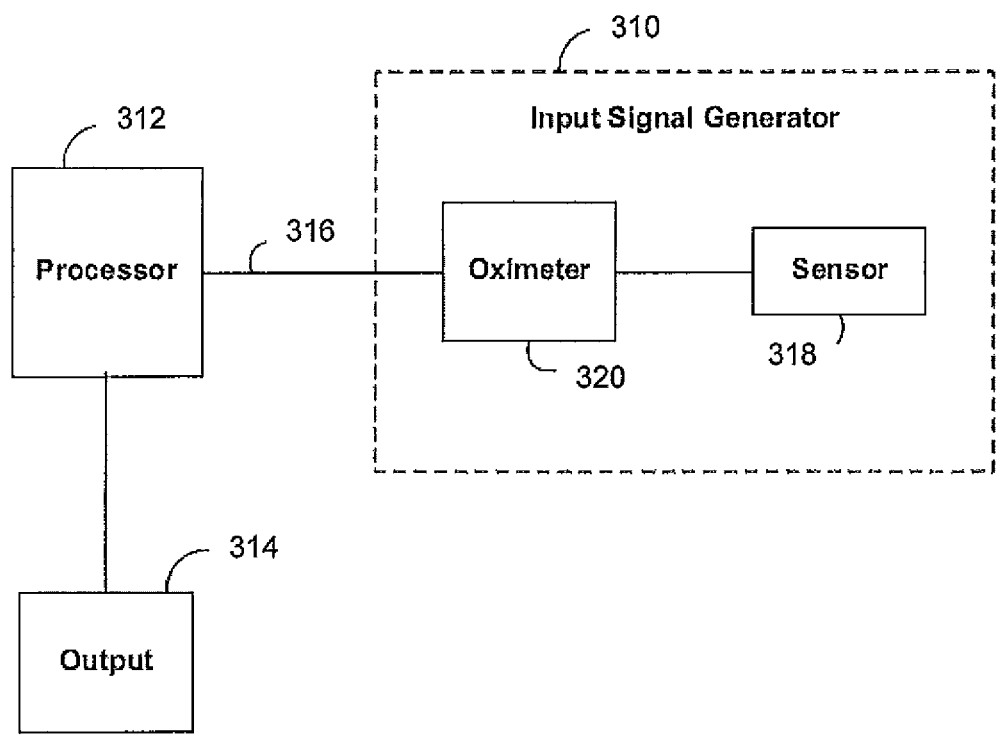
FIG. 3 is a block diagram of an illustrative signal processing system in accordance with some embodiments.

FIG. 3 is an illustrative processing system 300 in accordance with an embodiment. In an embodiment, input signal generator 310 generates an input signal 316. As illustrated, input signal generator 310 may include oximeter 320 (or similar device) coupled to sensor 318, which may provide as input signal 316, a PPG signal. It will be understood that input signal generator 310 may include any suitable signal source, signal generating data, signal generating equipment, or any combination thereof to produce signal 316.

Sensor 318 may be placed at a site on a patient, such as a fingertip, toe, forehead, or earlobe, or in the case of a neonate, across a foot. The morphology of the PPG signal, e.g., the features of the pulse wave, generated by sensor 318 may vary according to where sensor 318 is placed, thus requiring different signal processing techniques to be employed when analyzing the respective PPG signals. For instance, the PPG signal generated by a reflective sensor on the forehead generally has a more "rounded" appearance (e.g., fewer characteristic points) than the PPG signal generated by a sensor on the finger. The oximeter may pass light using a light source through blood perfused tissue and photoelectrically sense the absorption of light in the tissue. For example, oximeter 320 may measure the intensity of light that is received at sensor 318 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

In an embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform some or all of the calculations associated with the blood pressure monitoring methods of the present disclosure. For example, processor 312 may determine the time difference, T, between any two chosen characteristic points of a PPG signal obtained from input signal generator 310. Processor 312 may also be configured to apply equation (1) (or any other blood pressure equation using an elapsed time value) and compute estimated blood pressure measurements on a continuous or periodic basis. Processor 312 may also perform any suitable signal processing of signal 316 to filter signal 316, such as any suitable band-pass filtering, adaptive filtering, closed-loop filtering, and/or any other suitable filtering, and/or any combination thereof. For example, signal 316 may be filtered one or more times prior to or after identifying characteristic points in signal 316.

Processor 312 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. Processor 312 may be coupled to a calibration device (not shown) that may generate or receive as input reference blood pressure measurements for use in calibrating CNIBP calculations.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 212 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 300 may be incorporated into system 10 (FIGS. 1 and 2) in which, for example, input signal generator 310 may be implemented as parts of sensor 12 and monitor 14 and processor 312 may be implemented as part of monitor 14. In some embodiments, portions of system 300 may be configured to be portable. For example, all or a part of system 300 may be embedded in a small, compact object carried with or attached to the patient (e.g., a watch (or other piece of jewelry) or cellular telephone). In such embodiments, a wireless transceiver (not shown) may also be included in system 300 to enable wireless communication with other components of system 10. As such, system 10 may be part of a fully portable and continuous blood pressure monitoring solution.

Reliable blood pressure measurements may be derived from a PPG signal obtained from a single sensor or probe. In some embodiments, the constants a and b in equation (1) above may be determined by performing a calibration. The calibration may involve taking a reference blood pressure reading to obtain a reference blood pressure $P_0$, measuring the elapsed time $T_0$ corresponding to the reference blood pressure, and then determining values for both of the constants a and b from the reference blood pressure and elapsed time measurement. Calibration may be performed at any suitable time (e.g., once initially after monitoring begins) or on any suitable schedule (e.g., a periodic or event-driven schedule).

In some embodiments, the calibration may include performing calculations mathematically equivalent to $$a = c_1 + \frac{c_2(P_0 - c_1)}{\ln(T_0) + c_2} \quad (2)$$

and $$b = \frac{P_0 - c_1}{\ln(T_0) + c_2} \quad (3)$$

to obtain values for the constants a and b, where $c_1$ and $c_2$ are predetermined constants that may be determined, for example, based on empirical data.

In other embodiments, determining the plurality of constant parameters in the multi-parameter equation (1) may include performing calculations mathematically equivalent to $$a = P_0 - (c_3 T_0 + c_4)\ln(T_0) \quad (4)$$

and $$b = c_3 T_0 + c_4 \quad (5)$$

where a and b are first and second parameters and $c_3$ and $c_4$ are predetermined constants that may be determined, for example, based on empirical data.

In some embodiments, the multi-parameter equation (1) may include a non-linear function which is monotonically decreasing and concave upward in a manner specified by the constant parameters.

As mentioned above, multi-parameter equation (1) may be used to determine estimated blood pressure measurements from the time difference, T, between two or more characteristic points of a PPG signal. In some embodiments, the PPG signals used in the CNIBP monitoring techniques described herein are generated by a pulse oximeter or similar device.

The present disclosure may be applied to measuring systolic blood pressure, diastolic blood pressure, mean arterial pressure (MAP), or any combination of the foregoing on an on-going, continuous, or periodic basis. U.S. patent application Ser. No. 12/242,238 filed Sep. 30, 2008, which is hereby incorporated by reference herein in its entirety, discloses some techniques for continuous and non-invasive blood pressure monitoring that may be used in conjunction with the present disclosure.

Figure 4:
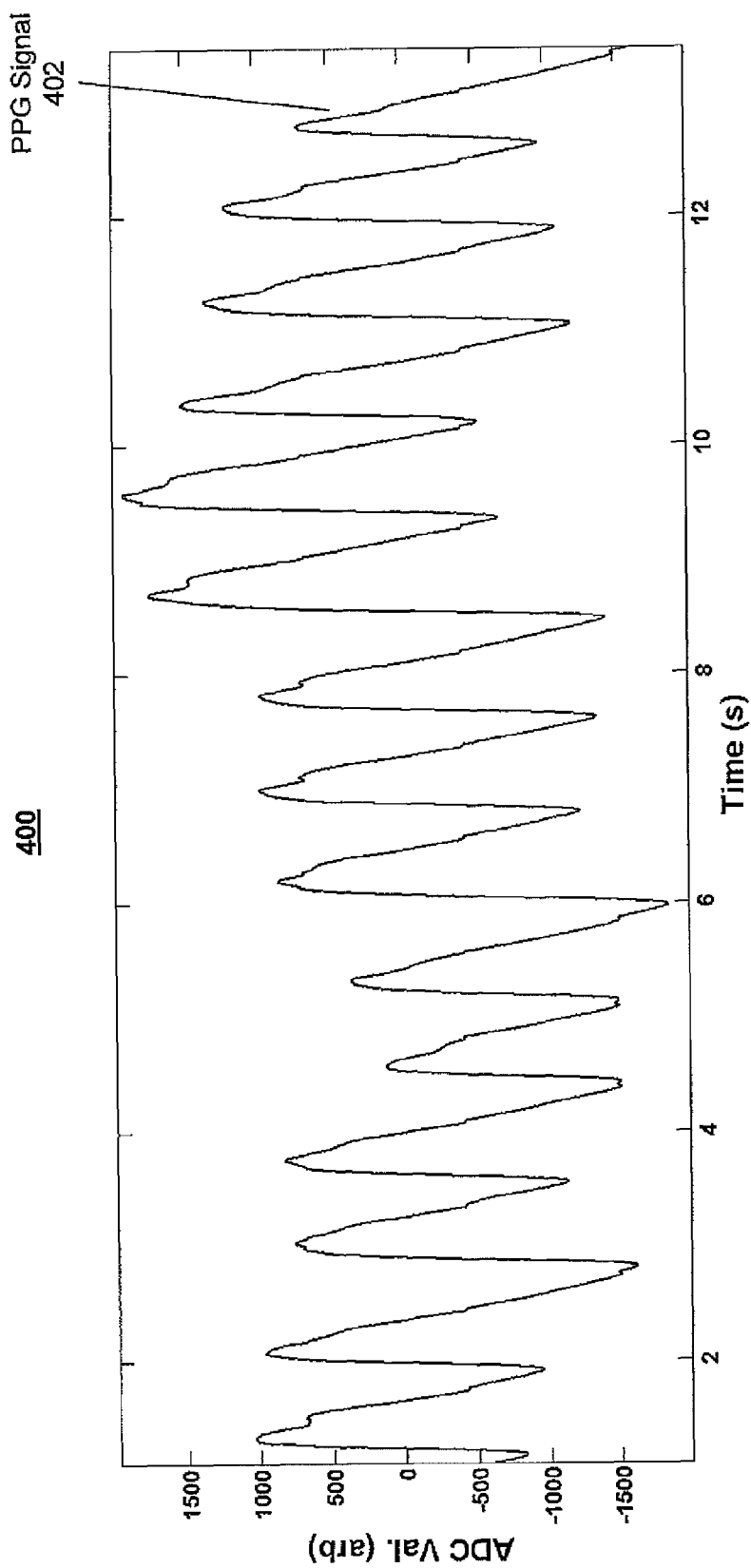
FIG. 4 shows an illustrative PPG signal in accordance with an embodiment.

FIG. 4 shows illustrative PPG signal 400. As described above, in some embodiments PPG signal 400 may be generated by a pulse oximeter or similar device positioned at any suitable location of a subject's body, e.g., the forehead, toe, finger, chest, or ear. For example, signal 400 is typical of an unfiltered PPG signal generated by a pulse oximeter positioned on a subject's finger. Furthermore, PPG Signal 400 may be detected by microprocessor 48 (FIG. 2) and/or processor 312 (FIG. 3) in CNIBP monitoring or pulse oximetry system 10. Notably, PPG signal 400 may be generated using only a single sensor or probe attached to a suitable location on the subject's body, e.g., on the patient's finger, toe, forehead, or earlobe.

Characteristic points in a PPG signal (e.g., PPG signal 400) may be identified in a number of ways, and using any suitable signal processing techniques. These characteristic points may be identified on the detected PPG signal, or a filtered version of the PPG signal. The detected PPG signal may be filtered to allow for easier identification of characteristic points, thereby improving results. The PPG signal (e.g., PPG signal 400) may be filtered one or more times using any combination of suitable filters. For example, microprocessor 48 (FIG. 2) and/or processor 312 (FIG. 3) may implement various types of digital (e.g., Finite Impulse Response (FIR) or Infinite Impulse Response (IIR) filters) or analog filters (e.g., Butterworth, Chebyshev, or Elliptical filters), using, for example, low pass, high-pass, and band-pass filters in order to process the detected PPG signal before identifying characteristic points. For instance, in some embodiments, the PPG signal is first filtered using a low-pass or band-pass filter, and may subsequently be filtered using a high-pass filter. Embodiments of a suitable high-pass filter will be described below in reference to FIGS. 5-7.

In some embodiments, the turning points of the filtered PPG signal are used as characteristic points. Additionally or alternatively, points of inflection in the filtered PPG signal (or any suitable derivative thereof) may also be used as characteristic points of the filtered PPG signal. The time difference, T, in the above equations (see, e.g., equation (1)) may also be computed. T may correspond to the time it takes the pulse wave to travel a predetermined distance (e.g., a distance from the sensor or probe to a reflection point and back to the sensor or probe). Characteristic points in the filtered PPG signal may also include the time between various peaks in the filtered PPG signal and/or in some derivative of the filtered PPG signal. For example, in some embodiments, the time difference, T, may be calculated between the maximum peak of the filtered PPG signal and the second peak in the filtered PPG signal. Any other suitable time difference between any suitable characteristic points in the filtered PPG signal (e.g., PPG signal 400) or any derivative of the filtered PPG signal may be used as T in other embodiments.

In some embodiments, the time difference between the adjacent peaks in the filtered PPG signal, the time difference between the adjacent valleys in the filtered PPG signal, or the time difference between any combination of peaks and valleys, can be used as the time difference T. As such, adjacent peaks and/or adjacent valleys in the filtered PPG signal (or in any derivative thereof) may also be considered characteristics points. In some embodiments, these time differences may be divided by the actual or estimated heart rate to normalize the time differences.

A patient's blood pressure may be monitored continuously using a moving average filtered PPG signal. PPG signal detection means may include a pulse oximeter (or other similar device) and associated hardware, software, or both. A processor may continuously analyze the signal from the PPG signal detection means in order to continuously monitor a patient's blood pressure.

In some embodiments, past blood pressure measurements may be used to scale current and future measurements. For example, to avoid large swings in detected blood pressure a running or moving blood pressure average may be maintained. Detected blood pressure values outside some pre-defined threshold of the moving average may be ignored in some embodiments. Additionally or alternatively, detected blood pressure values outside some pre-defined threshold of the moving average may automatically signal a recalibration event.

According to some embodiments, one or more calibration (or recalibration) steps may be employed by measuring the patient's blood pressure (or a reference blood pressure), $P_0$, and then measuring the corresponding elapsed time, $T_0$, between the chosen characteristic points in the PPG signal, as described in the calibration equations (2)-(5) above. Updated or refined values for constants a and b of equation (1) (or other suitable blood pressure equation) may then be computed based on the calibration. Calibration may be performed once, initially at the start of the continuous monitoring, or calibration may be performed on a regular or event-driven schedule. In some embodiments, calibration may also include changing the characteristic points used to compute the time difference, T. For example, several different blood pressure determinations may be made in parallel using different sets of characteristic points. The set of characteristic points that yields the most accurate blood pressure reading during the calibration period may then be used as the new set of characteristic points. As such, the characteristic points of the PPG signal used in the blood pressure determination may be modified on-the-fly and may vary during a single monitoring session. Such an adaptive approach to selecting characteristic points in the PPG signal may help yield more accurate blood pressure readings.

Figure 5:
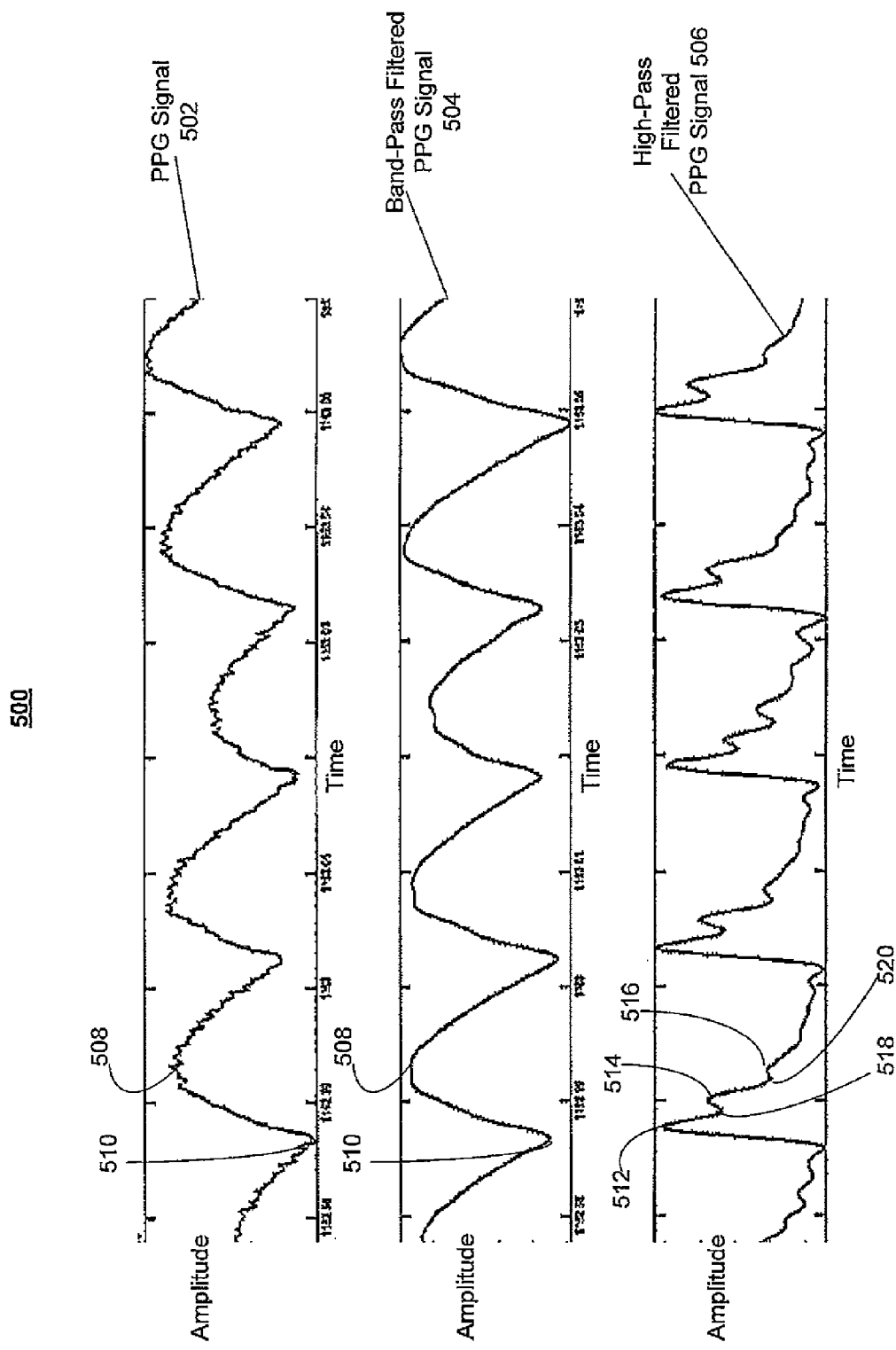
FIG. 5 shows an illustrative PPG signal, a band-pass filtered PPG signal, and a high-pass filtered PPG signal in accordance with an embodiment.

FIG. 5 shows a graph 500 with an illustrative PPG signal 502, a band-pass filtered PPG signal 504 derived from signal 502, and a high-pass filtered PPG signal 506 derived from signal 502. As described above, in some embodiments PPG signal 502 may be generated by a pulse oximeter or similar device (e.g., CNIBP monitoring or pulse oximetry system 10 of FIG. 1) positioned at any suitable location of a subject's body, e.g., the forehead, toe, finger, chest, or earlobe. Furthermore, PPG Signal 502 may be received or detected by microprocessor 48 (FIG. 2) and/or processor 312 (FIG. 3) in CNIBP monitoring or pulse oximetry system 10. As mentioned above, the morphology of the PPG signal, e.g., the features of the pulse wave, may vary according to the site on the patients' body where the sensor is placed. For instance, PPG signal 502 may be generated by a reflective sensor on the forehead generally giving it a more "rounded" appearance (e.g., fewer characteristic points) than PPG signal 400 of FIG. 4, which may be generated by a sensor on the finger. The particular morphology of PPG signal 502, including peak 508 and valley 510, may be a result of the complex path(s) taken by propagating pulse waves to the measurement site. For instance, in the forehead, the PPG signal morphology may include anastomeses between the internal and external carotid arteries through positions around the location of the eye.

Filtered PPG signal 504 may be generated from signal 502 using a variety of filtering approaches. In an embodiment, PPG signal 502 may be low-pass filtered with a suitable cut-off frequency (e.g., approximately 5-10 Hz) and then high-pass filtered with a suitable high-pass filter cut-off frequency (e.g., approximately 0.5 Hz) to generate filtered PPG signal 504. Alternatively, a band-pass filter with suitable band-pass frequencies (e.g., approximately 0.5-10 Hz) may be used to filter PPG signal 502. In this manner, the fundamental pulse frequency and other salient features of the PPG signal 502 may be preserved in filtered PPG signal 504. In general, the PPG signal (e.g., PPG signal 502) may be filtered one or more times using any combination of suitable filters. For example, microprocessor 48 (FIG. 2) and/or processor 312 (FIG. 3) of CNIBP monitoring or pulse oximetry system 10 (FIG. 1) may implement various types of digital filters (e.g., Finite Impulse Response (FIR) or Infinite Impulse Response (IIR) filters) or analog filters (e.g., Butterworth, Chebyshev, or Elliptical filters).

For some PPG signals (e.g., PPG signal 502) that may have been generated at a site with complex pulse propagation paths, e.g., the forehead, it may be advantageous to high-pass filter the PPG signal using a cut-off frequency $f_c$ that is substantially higher than the fundamental pulse frequency. Filtered PPG signal 506 may be generated from signal 502 using a variety of filtering approaches. As with filtered PPG signal 504, filtered PPG signal 506 may be generated by filtering PPG signal 502 one or more times using any combination of suitable filters. For example, microprocessor 48 (FIG. 2) and/or processor 312 (FIG. 3) of CNIBP monitoring or pulse oximetry system 10 (FIG. 1) may implement various types of digital filters (e.g., Finite Impulse Response (FIR) or Infinite Impulse Response (IIR) filters) or analog filters (e.g., Butterworth, Chebyshev, or Elliptical filters). In an embodiment, PPG signal 502 may be high-pass filtered with a cut-off frequency $f_c$ falling approximately between 0.75 Hz and 15 Hz, to obtain filtered PPG signal 506. For example, the cut-off frequency may be approximately 7.5 Hz. In an alternative embodiment, PPG signal 502 may be filtered one or more times using a digital or analog differentiation filter to obtain filtered PPG signal 506. Filtered PPG signal 506 may contain peaks 512, 514 and 516, and valleys 518 and 520. These peaks and valleys may be identified by microprocessor 48 (FIG. 2) and/or processor 312 (FIG. 3) of CNIBP monitoring or pulse oximetry system 10 (FIG. 1) as characteristic points of the filtered PPG signal 506. In turn, the identified characteristic points may be used to compute blood pressure measurements.

In some embodiments, PPG signal 502 may be high-pass filtered with a cut-off frequency $f_c$ selected to be greater than a typical pulse rate, e.g., 0.75 Hz to 2.5 Hz, but less than about 15 Hz.

In some embodiments, PPG signal 502 may be high-pass filtered with a cut-off frequency $f_c$ selected to be greater than a subject's pulse rate. A subject's pulse rate may be computed in any suitable manner. In some embodiments, the subject's pulse rate may be computed using a time-domain analysis of PPG signal 502. In an embodiment, onset times of each pulse in the PPG signal may be detected, and the pulse rate in beats per minute may be computed as 60 divided by the difference of consecutive onset times. Alternatively, the pulse rate in beats per minute may be computed as 60 divided by the difference of the average or mean of a set of consecutive onset times in the PPG signal 502.

In some embodiments, the subject's pulse rate may be computed using a frequency-domain analysis of PPG signal 502. In some embodiments, a Fourier transform of a suitable length window of the PPG signal 502 may be computed. The pulse frequency may then be detected from the computed Fourier transform. In an embodiment, the pulse frequency may be selected to be the frequency corresponding to a peak in the Fourier transform in the typical pulse frequency range, e.g., 0.75 Hz to 2.5 Hz. In an embodiment, the pulse frequency may be selected to be the average of the frequencies corresponding to peaks in the Fourier transform in the typical pulse frequency range, e.g., 0.75 Hz to 2.5 Hz, of two consecutive windows of PPG signal 502.

In some embodiments, the subject's pulse rate may be updated or computed continuously or periodically, e.g., at intervals of 15 seconds to 5 minutes, using a suitable time-domain or frequency-domain analysis of the PPG signal 502 as described above. In an embodiment, each time the pulse rate is computed, the cut-off frequency $f_c$ may be updated or re-selected such that it remains greater than the subject's computed pulse rate. For example, the cut-off frequency $f_c$ may be set approximately equal to the computed pulse rate, to a frequency that is a predetermined amount (e.g., 0.5 Hz, 1 Hz, 2 Hz, 3 Hz, 4 Hz, 5 Hz, 10 Hz, 15 Hz, etc.) higher than the computed pulse rate, or to frequency selected from a list of available filtering frequencies (e.g., 0.75 Hz, 1 Hz, 2 Hz, 3 Hz, 4 Hz, 5 Hz, 7.5 Hz, 10 Hz, 15 Hz, etc.). In an embodiment, the cut-off frequency $f_c$ may be updated or re-selected based on instantaneous values of pulse rate or a filtered pulse rate (e.g., a running average).

Those skilled in the art will appreciate that other time-domain and/or frequency-domain methods for computing pulse rate other than those described above may be employed.

The accuracy and reliability enabled by high-pass filtering with a cut-off frequency $f_c$, substantially higher than the fundamental pulse frequency, including the ability to identify characteristic points in a PPG signal may be beneficial for the derivation of physiological parameters such as CNIBP which may depend on accurate determination of pulse transit or first pulse arrival times. Additionally or alternatively, the high-pass filtered PPG signal may enable the differentiation or disambiguation between low-frequency components of a PPG signal (e.g., venous flow) and high-frequency components of the PPG signal (e.g., arterial components). PPG signals 502 and 504 may be dominated by, or at least preserve a significant portion of, low-frequency components, pertinent to the frequency of occurrence of PPG pulses and other physiology of lower frequencies (for example changes in vascular tone), while high-pass filtered PPG signal 506 may be primarily dominated by, or at least preserve a significant portion of, high-frequency components pertinent to the component features of individual PPG pulses (for example pulse arrival time, and notch positions and numbers).

Notably, the pulse transit time computed from signals 502 or 504 may be relatively unreliable and inaccurate, when compared to the pulse transit time computed from filtered PPG signal 506. The relatively rounded shape of signals 502 and 504 can make it relatively difficult to identify with accuracy and reliably characteristic points in the signal that may be used to measure the pulse transit time. In an embodiment, the pulse transit time for PPG signal 502 may be computed as the time difference between peak 508 and valley 510. For filtered PPG signal 506, the pulse transit time may be computed using any of characteristic points 512, 514, 516, 518, and 520. The pulse transit time obtained from high-pass filtered signal 506 in this manner would be much more accurate and reliable than that obtained from PPG signal 502. For instance, the pulse transit time calculated from signal 502 or 504 would be larger and less accurate than that computed from signal 506. One reason for the higher accuracy and reliability is that the use of high-pass filtered PPG signal 506 allows for identification of the characteristic points with higher accuracy than the use of signals 502 and 504, thereby allowing for a more accurate determination of pulse transit time or other time differences computed from the identified characteristic points. In an embodiment, high-pass filtered PPG signal 506 may allow for more accurate determination of the arrival time of the first pulse at the sensor site, whereas points such as 508 and 510 make such a determination more difficult and less accurate. For instance, the pulse transit time calculated from signal 502 or 504 would be larger and less accurate than that computed from signal 506.

In an embodiment, pulse transit time or any other suitable time difference may be computed as the time difference between an identified characteristic point from the filtered PPG signal derived from a PPG signal generated by a first sensor and a corresponding identified characteristic point from the filtered PPG signal derived from a PPG signal generated by a second sensor. The first and second sensors may be located at different sites on the patient's body, e.g., one sensor on the patient's finger and another sensor on the patient's toe. In other embodiments, such as those described in more detail in U.S. patent application Ser. No. 12/242,238 filed Sep. 30, 2008, which is hereby incorporated by reference herein in its entirety, a single sensor may be used to generate a PPG signal from which two or more suitable characteristic points may be identified. A time difference may then be computed from the identified characteristic points. Those skilled in the art will appreciate that methods other than the literal measurement of distance between equivalent fiducial points may be used for determining pulse transit times. For example the cross-correlation of high pass filtered pulses, or pulse trains, from the two sites may be used to identify time delays.

Figure 6:
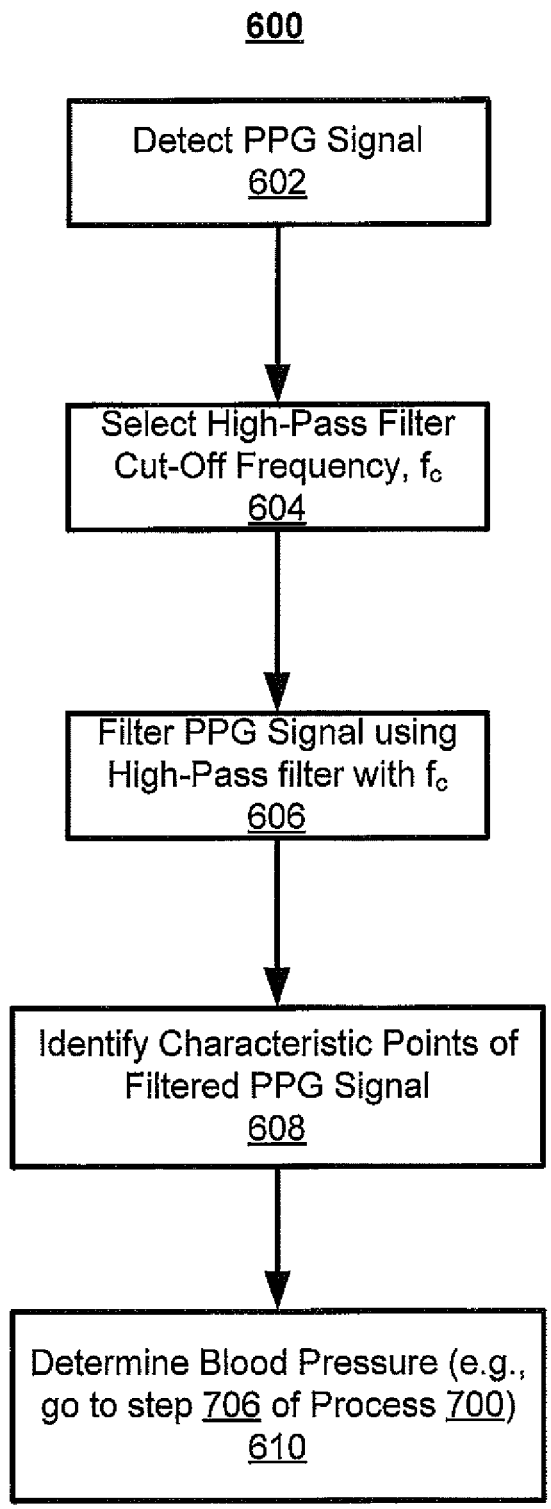
FIG. 6 shows an illustrative process for high-pass filtering a PPG signal in accordance with an embodiment.

FIG. 6 shows an illustrative process 600 for high-pass filtering a PPG signal. At step 602, a PPG signal is detected from a patient. For example, monitor 14 (FIGS. 1 and 2) may be used to detect a PPG signal from patient 40 (FIG. 2) using, for example, sensor 12 (FIGS. 1 and 2). The sensor may be located at any suitable site on the patient, e.g., forehead, toe, finger, or chest. The PPG signal may be detected by microprocessor 48 (FIG. 2) and/or processor 312 (FIG. 3) of CNIBP monitoring or pulse oximetry system 10 (FIG. 1). A user interacting with monitor 14 (FIGS. 1 and 2) may then select a suitable cut-off frequency $f_c$ for the high-pass filter. If a user does not make such a selection, microprocessor 48 (FIG. 2) and/or processor 312 (FIG. 3) of CNIBP monitoring or pulse oximetry system 10 (FIG. 1) may retrieve a previous user-selected cut-off frequency from memory or a storage device (e.g., ROM 52 or RAM 54 of monitor 14 (FIG. 2)), or may use a cut-off frequency stored in memory or a storage device (e.g., ROM 52 or RAM 54 of monitor 14 (FIG. 2)). In an embodiment, suitable cut-off frequencies may be greater than 0.75 Hz, or less than 15 Hz. For example, the cut-off frequency may be approximately 7.5 Hz.

In an embodiment, the cut-off frequency $f_c$ is selected to be greater than a typical pulse rate, e.g., 0.75 Hz to 2.5 Hz, but less than 15 Hz. In some embodiments, the cut-off frequency $f_c$ is selected to be greater than a subject's pulse rate, which may be computed in any suitable manner as described above in relation to FIG. 5. The subject's pulse rate may also be updated or computed continuously or periodically, e.g., at intervals of 15 seconds to 5 minutes, using a suitable time-domain or frequency-domain analysis of windows of the detected PPG signal as described above. Each time the pulse rate is computed, the cut-off frequency $f_c$ may be updated or re-selected such that it remains greater than the subject's computed pulse rate. For example, the cut-off frequency $f_c$ may be set approximately equal to the computed pulse rate, to a frequency that is a predetermined amount (e.g., 0.5 Hz, 1 Hz, 2 Hz, 3 Hz, 4 Hz, 5 Hz, 10 Hz, 15 Hz, etc.) higher than the computed pulse rate, or to frequency selected from a list of available filtering frequencies (e.g., 0.75 Hz, 1 Hz, 2 Hz, 3 Hz, 4 Hz, 5 Hz, 7.5 Hz, 10 Hz, 15 Hz, etc.). In an embodiment, the cut-off frequency $f_c$ may be updated or re-selected based on instantaneous values of pulse rate or a filtered pulse rate (e.g., a running average).

After a suitable cut-off frequency $f_c$ has been selected or retrieved from memory or a storage device, the detected PPG signal is filtered using a high-pass filter with the selected cut off frequency $f_c$ (step 606). In practice, microprocessor 48 (FIG. 2) and/or processor 312 (FIG. 3) of CNIBP monitoring or pulse oximetry system 10 (FIG. 1) may implement various types of digital high-pass (e.g., Finite Impulse Response (FIR) or Infinite Impulse Response (IIR) filters) or analog high-pass filters (e.g., Butterworth, Chebyshev, or Elliptical filters). In an alternative embodiment, microprocessor 48 (FIG. 2) and/or processor 312 (FIG. 3) of CNIBP monitoring or pulse oximetry system 10 (FIG. 1) may use a differentiation filter or a sequence of differentiation filters to process the detected PPG signal.

At step 608, two or more characteristic points from a filtered PPG signal are identified. For example, microprocessor 48 (FIG. 2) may analyze the filtered PPG signal and identify various candidate characteristic points in the filtered PPG signal. As described above, peaks, valleys, turning points, and points of inflection in either the filtered PPG signal or any suitable derivative of the filtered PPG signal may be used as suitable characteristic points in some embodiments. As described above, microprocessor 48 (FIG. 2) and/or processor 312 (FIG. 3) of CNIBP monitoring or pulse oximetry system 10 (FIG. 1) may identify such characteristic points using any suitable signal processing techniques.

After the two or more characteristic points are identified in the filtered PPG signal, at step 610 a blood pressure measurement is determined. This blood pressure measurement may be determined using process 700 (FIG. 7) as described below.

In practice, one or more steps shown in process 600 may be combined with other steps, performed in any suitable order, performed in parallel (e.g., simultaneously or substantially simultaneously), or removed.

Figure 7:
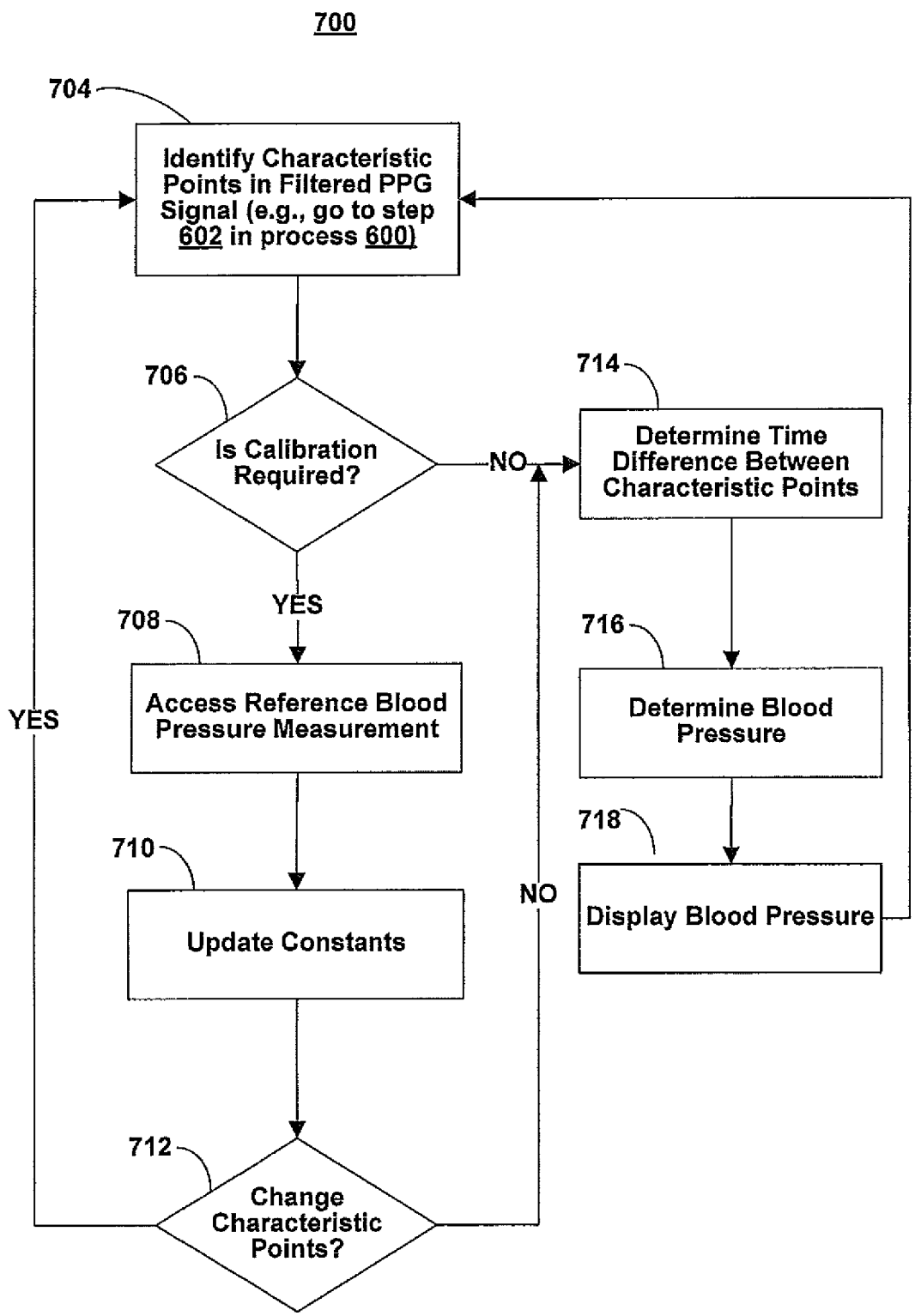
FIG. 7 shows an illustrative process for determining blood pressure from identified characteristic points obtained through process 600 of FIG. 6 of a filtered PPG signal in accordance with an embodiment.

FIG. 7 shows an illustrative process 700 for determining blood pressure from identified characteristic points of a filtered PPG signal. The filtered PPG signal may be a high-pass filtered PPG signal generated by microprocessor 48 (FIG. 2) and/or processor 312 (FIG. 3) of CNIBP monitoring or pulse oximetry system 10 (FIG. 1) using process 600 of FIG. 6. At step 704, two or more characteristic points from a filtered PPG signal are identified. Filtered PPG signal may be generated using process 600 (FIG. 6) from a PPG signal that is detected from a patient. For example, monitor 14 (FIGS. 1 and 2) may be used to detect a PPG signal from patient 40 (FIG. 2) using, for example, sensor 12 (FIGS. 1 and 2), and process 600 (FIG. 6) may be used to identify the characteristic points of the filtered PPG signal.

After the characteristic points are identified in the filtered PPG signal, at step 706 a determination is made whether a calibration is required or signaled (or should be signaled or required). As described above, a calibration may be performed once after monitoring initialization or calibration may be performed periodically on any suitable schedule. For example, a calibration event may be signaled by microprocessor 48 (FIG. 2) after blood pressure measurements have exceeded some predefined threshold window or some standard deviation from the mean or moving average of previous measurements. As another example, a calibration event may be signaled by microprocessor 48 (FIG. 2) after the passage of some predetermined length of time from the last calibration event. In such embodiments, microprocessor 48 (FIG. 2) may access a timer or clock and automatically signal calibration events on a periodic schedule.

If calibration has been signaled or required, at step 708 one or more reference blood pressure measurements may be accessed. For example, calibration device 80 (FIGS. 1 and 2) may continuously or periodically generate reference blood pressure measurements for use in calibration. These reference blood pressure measurements may be derived from any suitable invasive or non-invasive blood pressure monitoring technique. The measurements may also be accessed from any suitable storage device, or the measurements may be manually inputted by an operator (e.g., if read from an external monitoring or measurement device).

After the reference blood pressure measurement or measurements are accessed, at step 710 constant parameters may be updated. For example, one or more of constants a and b of equation (1) above may be updated. Any other suitable constants or parameters (of any other suitable blood pressure equation) may be updated in other embodiments. At step 712, a determination is made whether or not to change characteristic points, e.g., whether or not to identify one or more other suitable characteristic points. For example, microprocessor 48 (FIG. 2) may dynamically alter the set of characteristic points identified at step 704. As described above, process 600 (FIG. 6) may be used to identify the other suitable characteristic points of the filtered PPG signal. In some embodiments, multiple sets of characteristic points are identified in parallel and the set of characteristic points yielding the closest blood pressure measurement to the reference blood pressure measurement accessed at step 708 is selected as the new set of characteristic points. If a new set of characteristic points are identified, process 700 may return to step 704.

If the set of characteristic points is not changed at step 712 (or if no calibration is required at step 716), then process 700 may continue at step 714. At step 714, the time difference, T, between the identified characteristic points in the filtered PPG signal may be determined. For example, microprocessor 48 (FIG. 2) may compute the time difference between two adjacent peaks, two adjacent valleys, turning points, or points of inflection directly from the filtered PPG signal. Microprocessor 48 (FIG. 2) may also compute one or more derivatives of the filtered PPG signal and determine the time difference between any two characteristic points in any PPG, filtered PPG and derivative signals thereof.

Finally, at step 716, a blood pressure measurement may be determined based, at least in part, on the time difference determined at step 614. For example, equation (1) above (or any other blood pressure equation using an elapsed time between the arrival of corresponding points of a pulse signal or any other suitable computed time difference) may be used to compute estimated blood pressure measurements. The computed time difference between characteristic points in the PPG signal may be substituted for the elapsed time between the arrival of corresponding points of a pulse signal. After a blood pressure measurement is determined at step 716, process 700 may return to step 704 and identify new characteristic points of a filtered PPG signal (or access a new segment of a running filtered PPG signal). As such, process 700 may generate blood pressure measurements continuously.

After blood pressure measurements are determined, the measurements may be outputted, stored, or displayed in any suitable fashion (718). For example, multi-parameter patient monitor 26 (FIG. 1) may display a patient's blood pressure on display 28 (FIG. 1). Additionally or alternatively, the measurements may be saved to memory or a storage device (e.g., ROM 52 or RAM 54 of monitor 14 (FIG. 2)) for later analysis or as a log of a patient's medical history.

In practice, one or more steps shown in process 700 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for high-pass filtering a photoplethysmograph (PPG) signal used for determining a blood pressure measurement of a subject comprising:
   detecting the PPG signal;
   computing a pulse frequency of the subject;
   selecting a cut-off frequency for a high-pass filter based at least in part on the computed pulse frequency, such that the cut-off frequency is approximately equal to the computed pulse frequency;
   filtering the detected PPG signal with the high-pass filter;
   identifying at least one characteristic point in the filtered PPG signal; and
   determining, based at least in part on the at least one identified characteristic point, the blood pressure measurement.

2. The method of claim 1 wherein identifying at least one characteristic point in the filtered PPG signal comprises identifying at least one stationary point or inflection point of the filtered PPG signal.

3. The method of claim 1 wherein identifying at least one characteristic point in the filtered PPG signal comprises identifying a local turning point in the filtered PPG signal.

4. The method of claim 1 wherein identifying at least one characteristic point in the filtered PPG signal comprises identifying two peaks in the filtered PPG signal.

5. The method of claim 1 wherein determining, based at least in part on the at least one identified characteristic point, a blood pressure measurement comprises taking a natural logarithm of a time difference determined from the at least one identified characteristic point.

6. The method of claim 1 wherein determining, based at least in part on the on the at least one identified characteristic point, a blood pressure measurement comprises solving a multi-parameter equation, wherein the multi-parameter equation is $$p = a + b \cdot \ln(T)$$

where p is the determined blood pressure measurement, T is a time difference determined from the at least one identified characteristic point, and a and b are constants.

7. The method of claim 1 further comprising performing at least one calibration of the blood pressure measurement, the calibration based at least in part on a known reference blood pressure measurement.

8. The method of claim 1 wherein the cut-off frequency is less than 15 Hz.

9. A system for high-pass filtering a photoplethysmograph (PPG) signal used for determining a blood pressure measurement of a subject comprising:
   a sensor capable of generating the PPG signal; and
   a processor configured for:
      detecting the PPG signal;
      computing a pulse frequency of the subject;
      selecting a cut-off frequency for a high-pass filter based at least in part on the computed pulse frequency, such that the cut-off frequency is approximately equal to the computed pulse frequency;
      filtering the detected PPG signal with the high-pass filter;
      identifying at least one characteristic point in the filtered PPG signal; and
      determining, based at least in part on the at least one identified characteristic point, the blood pressure measurement.

10. The system of claim 9 wherein the sensor comprises a pulse oximeter.

11. The system of claim 9 wherein the processor is further configured for identifying at least one stationary point or inflection point of the filtered PPG signal.

12. The system of claim 9 wherein the processor is further configured for identifying a local turning point of the filtered PPG signal.

13. The system of claim 9 wherein the processor is further configured for identifying two peaks of the filtered PPG signal.

14. The system of claim 9 wherein the processor is further configured for determining, based at least in part on the at least one identified characteristic point, a blood pressure measurement by solving a multi-parameter equation, wherein the multi-parameter equation is $$p = a + b \cdot \ln(T)$$

where p is the determined blood pressure measurement, T is a time difference determined from the at least one identified characteristic point, and a and b are constants.

15. The system of claim 9 wherein the processor is further configured for performing at least one calibration of the blood pressure measurement, the calibration based at least in part on a known reference blood pressure measurement.

16. The system of claim 9 wherein the cut-off frequency is less than 15 Hz.

17. A method for high-pass filtering a photoplethysmograph (PPG) signal used for determining a blood pressure measurement of a subject comprising:
   detecting the PPG signal;
   computing a pulse frequency of the subject;
   selecting a cut-off frequency for a high-pass filter based at least in part on the computed pulse frequency, such that the cut-off frequency is a predetermined amount higher than the computed pulse frequency, wherein the predetermined amount is less than 0.5 Hz.;
   filtering the detected PPG signal with the high-pass filter;
   identifying at least one characteristic point in the filtered PPG signal; and
   determining, based at least in part on the at least one identified characteristic point, the blood pressure measurement.

* * * * *